(12) United States Patent
Oxman et al.

(10) Patent No.: US 7,134,875 B2
(45) Date of Patent: Nov. 14, 2006

(54) PROCESSES FOR FORMING DENTAL MATERIALS AND DEVICE

(75) Inventors: Joel D. Oxman, Minneapolis, MN (US); Bradley D. Craig, Cottage Grove, MN (US); Rajdeep S. Kalgutkar, St. Paul, MN (US); Marc Peuker, Schondorf (DE); Peter Bissinger, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 28 days.

(21) Appl. No.: 10/185,431

(22) Filed: Jun. 28, 2002

(65) Prior Publication Data

US 2004/0005524 A1 Jan. 8, 2004

(51) Int. Cl.
*A61C 5/04* (2006.01)
(52) U.S. Cl. .................................................. 433/226
(58) Field of Classification Search ................ 433/215, 433/222.1, 228; 522/4
See application file for complete search history.

(56) References Cited

U.S. PATENT DOCUMENTS

| | | | |
|---|---|---|---|
| 4,165,265 A * | 8/1979 | Nakabayashi et al. ......... 522/4 |
| 4,292,152 A | 9/1981 | Lechtken et al. |
| 4,298,738 A | 11/1981 | Lechtken et al. |
| 4,324,744 A | 4/1982 | Lechtken et al. |
| 4,356,296 A | 10/1982 | Griffith et al. |
| 4,385,109 A | 5/1983 | Lechtken et al. |
| 4,503,169 A | 3/1985 | Randklev |
| 4,516,195 A | 5/1985 | Gonser |
| 4,568,558 A | 2/1986 | Angrick et al. |
| 4,642,126 A | 2/1987 | Zador et al. |
| 4,652,274 A | 3/1987 | Boettcher et al. |
| 4,695,251 A | 9/1987 | Randklev |
| 4,710,523 A | 12/1987 | Lechtken et al. |
| 4,719,149 A | 1/1988 | Aasen et al. |
| 4,737,593 A | 4/1988 | Ellrich et al. |
| 4,771,084 A * | 9/1988 | Kubota et al. ................ 522/10 |
| 4,792,632 A * | 12/1988 | Ellrich et al. ................ 568/15 |
| 4,872,936 A | 10/1989 | Engelbrecht |
| 4,888,489 A | 12/1989 | Bryan |
| 5,063,257 A | 11/1991 | Akahane et al. |
| 5,076,844 A | 12/1991 | Fock et al. |
| 5,102,924 A * | 4/1992 | Williams et al. ............... 522/4 |
| 5,110,513 A | 5/1992 | Puvilland |
| 5,130,347 A | 7/1992 | Mitra |
| 5,147,204 A | 9/1992 | Patten et al. |
| 5,154,762 A | 10/1992 | Mitra et al. |
| 5,227,413 A | 7/1993 | Mitra |
| 5,256,447 A | 10/1993 | Oxman et al. |
| 5,367,002 A | 11/1994 | Huang et al. |
| 5,472,991 A | 12/1995 | Schmitt et al. |
| 5,501,727 A | 3/1996 | Wang et al. |
| 5,520,725 A | 5/1996 | Kato et al. |
| 5,525,648 A | 6/1996 | Aasen et al. |
| 5,545,676 A | 8/1996 | Palazzotto et al. |
| 5,856,373 A | 1/1999 | Kaisaki et al. |
| 5,859,089 A | 1/1999 | Qian |
| 5,871,360 A | 2/1999 | Kato |
| 5,925,715 A | 7/1999 | Mitra |
| 5,962,550 A | 10/1999 | Akahane et al. |
| 5,965,632 A | 10/1999 | Orlowski et al. |
| 5,980,253 A | 11/1999 | Oxman et al. |
| 6,008,264 A | 12/1999 | Ostler et al. |
| 6,030,606 A | 2/2000 | Holmes |
| 6,043,295 A | 3/2000 | Oxman et al. |
| 6,084,004 A | 7/2000 | Weinmann et al. |
| 6,184,339 B1 * | 2/2001 | Stansbury et al. .......... 528/407 |
| 6,187,833 B1 | 2/2001 | Oxman et al. |
| 6,187,836 B1 | 2/2001 | Oxman et al. |
| 6,251,963 B1 | 6/2001 | Köhler et al. |
| 6,306,926 B1 | 10/2001 | Bretscher et al. |
| 6,387,981 B1 | 5/2002 | Zhang et al. |
| 2001/0032985 A1 | 10/2001 | Bhat et al. |
| 2002/0016378 A1 | 2/2002 | Jin et al. |

FOREIGN PATENT DOCUMENTS

| | | |
|---|---|---|
| DE | 2846471 A1 | 5/1980 |
| DE | 196 19 154 | 6/1997 |
| DE | 29714686 U1 | 12/1997 |
| DE | 196 36 266 | 3/1998 |
| DE | 10065903 A1 | 1/2002 |
| EP | 0173567 A2 | 3/1986 |
| EP | 0201031 B1 | 11/1986 |
| EP | 0201778 B1 | 11/1986 |
| EP | 0325286 A2 | 7/1989 |
| EP | 0325286 A3 | 7/1989 |
| EP | 0325286 B1 | 7/1989 |
| EP | 0373384 B1 | 6/1990 |

(Continued)

OTHER PUBLICATIONS

Ciba Speciality Chemicals Coating Effects, "Ciba® CGI 403 Photoinitiator A Comparison of CGI 403 to Irgacure® 819," Ciba Specialty Chemicals Corporation, Tarrytown, NY, 5 pgs. (Feb. 8, 2001).

(Continued)

*Primary Examiner*—Melba Bumgarner
(74) *Attorney, Agent, or Firm*—Sean J. Edman (57) ABSTRACT

Processes for forming dental materials that include applying a first hardenable dental composition (e.g., a dental adhesive) to a surface followed by applying a second hardenable dental composition (e.g., a dental composite) to the first hardenable dental composition on the surface. The first and second hardenable dental compositions are hardened such that the second hardenable composition is substantially completely hardened prior to complete hardening of the first hardenable composition.

25 Claims, 2 Drawing Sheets

FOREIGN PATENT DOCUMENTS

| | | |
|---|---|---|
| EP | 0 879 582 | 11/1998 |
| EP | 0 998 880 | 5/2000 |
| EP | 1 031 326 | 8/2000 |
| EP | 1 310 218 | 5/2003 |
| WO | WO 99/22667 | 5/1999 |
| WO | WO 00/38619 | 7/2000 |
| WO | WO 00/42092 | 7/2000 |
| WO | WO 01/07444 A1 | 2/2001 |
| WO | WO 01/30304 A1 | 5/2001 |
| WO | WO 01/30305 A1 | 5/2001 |
| WO | WO 01/30306 A1 | 5/2001 |
| WO | WO 01/30307 A1 | 5/2001 |
| WO | WO 01/64129 A1 | 9/2001 |
| WO | WO 01/92271 A1 | 12/2001 |

OTHER PUBLICATIONS

Lopes et al., "Effect of a new resin inlay/onlay restorative material on cuspal reinforcement," *Quintessence Int.*, vol. 22(8):641-645 (Aug. 1991).

Mathis et al., "Properties of a New Glass Ionomer/Composite Resin Hybrid Restorative," Abstract No. 51, *J. Dent Res.*, vol. 66:113 (no month indicated, 1987).

Morin et al., "Cusp Reinforcement by the Acid-etch Technique," *J Dent Res.*, vol. 63(8):1075-1078 (Aug. 1984).

Morin et al., "Biophysical stress analysis of restored teeth: experimental strain measurement," *Dent Mater.*, vol. 4(1):41-48 (Feb. 1988).

Product Information Sheet, "3MConcise™ Restorative Material, Instructions for use" 3M Dental Products, St. Paul, MN, 1 pg. (Oct. 2000).

Product Information Sheet, "3M Filtek™ Z250 Universal Restorative, Instructions for use" 3M Dental Products, St. Paul, MN, 1 pg. (Nov. 1998).

Product Information Sheet, "3M Filtek™ Z250 Universal Restorative, Instructions for use" 3M Dental Products, St. Paul, MN, 1 pg. (Jan. 1999).

Product Information Sheet, "3M Single Bond Dental Adhesive System, Instructions for use" 3M Dental products, St. Paul, MN, 2 pgs. (Feb. 2000).

Product Information Brochure, "The dual phase light curing for time saving cementing ESPE TULUX-CEM," Gernab Product Information Brochure with translation, ESPE, Factory for Pharmaceutical Preparations GmbH & Co., Seefeld/Oberbayern, West Germany, 12 pgs. (no month or year indicated).

\* cited by examiner

PROCESSES FOR FORMING DENTAL MATERIALS AND DEVICE

TECHNICAL FIELD

This invention relates to processes for forming dental materials from hardenable dental compositions involving generally sequential hardening.

BACKGROUND

Hardenable polymeric materials are used in a wide variety of dental applications, including composites, filling materials, restoratives, cements, adhesives, and the like. Often, such materials shrink upon hardening. This is particularly problematic when the material is in a constrained environment, as in a dental filling or restorative, for example. Dimensional changes upon shrinkage while in a constrained environment can generate a strain within the material that is typically converted into a stress on the surrounding environment (e.g., tooth). Such forces can result in interfacial failures between the tooth and the polymeric material resulting in a physical gap and subsequent microleakage into the tooth cavity. Alternatively, such forces can lead to fractures within the tooth and/or the composite.

Generally, conventional processes of hardening polymeric dental materials involve a composite held in place on an oral surface with an adhesive and involve hardening the adhesive and then subsequently hardening the composite material. More specifically, conventional methods utilize one or more of the following steps: surface treatment of the tooth (e.g., etching, priming), application of a hardenable adhesive to the tooth surface, curing of the adhesive, placement of a composite material (e.g., restorative) on the hardened adhesive, and curing of the composite material. Such methods also typically utilize a blue light source emitting between approximately 380 nm to 520 nm to induce hardening. Photocurable dental compositions are preferably polymerized within a range of about 380 nm to 520 nm for the following reasons: 1) photoactivation utilizing UV photoinitiators or sensitizers (such as benzoin alkyl ethers, acetophenone derivatives, benzophenone and the like) that absorb light at wavelengths less than about 380 nm are generally considered to be unsafe due to the shortwavelength radiation; 2) photoinitiators or photosensitizers (such as eosin dyes, rose bengal, methylene blue and the like) that absorb light at wavelengths greater than about 520 nm are generally unsuitable due to their highly colored nature (red to blue in color) in a spectral region which is esthetically unsuitable for teeth which are generally white to slightly yellow. 3) the preferred sensitizers and initiators for dental compositions which absorb blue light between about 380 nm to 520 nm are typically pale yellow to yellow in color which provides clinically acceptable materials in terms of the esthetics of the hard tissues. Therefore, the practical limitations described have led to nearly exclusive usage of blue light. Thus, there is a need for methods of hardening dental materials, e.g., dental adhesives and dental composites, that reduce the amount of stress placed on the dental material and the surrounding environment during or after hardening.

SUMMARY OF THE INVENTION

The present invention provides processes for hardening (e.g., curing by polymerization, crosslinking, ionic reaction, or other chemical reaction) hardenable compositions involving a generally sequential hardening of the compositions. Such processes are particularly useful in dental applications, such as dental sealants, dental adhesives, dental cements, dental composites, dental restoratives, and dental prostheses, for example. The processes of the present invention typically result in a reduction in the amount of stress placed on the dental material and surrounding environment during and/or after hardening of the material.

Generally, the processes of the present invention involve a first step of initiating hardening of a second composition that is in contact with a first composition that is in contact with a dental surface (e.g., tooth surface or bone). Subsequently, either while the second composition is hardening (e.g., polymerizing) or after it is substantially completely hardened, the processes involve a second step of initiating hardening of the first composition. Typically, the hardening steps can be carried out through a chemical curing mechanism or a photopolymerization mechanism, for example.

In one embodiment, the present invention provides a process for forming a dental material adhered to a surface that includes: applying a first hardenable dental composition to the surface, wherein the first hardenable composition includes a first photoinitiator that absorbs radiation within a range of about 380 nm to about 520 nm (blue light); applying a second hardenable dental composition to the first hardenable composition on the surface, wherein the second hardenable composition includes a second photoinitiator that absorbs radiation within a range of about 380 nm to about 520 nm; irradiating the second hardenable composition with radiation within a range of about 380 nm to about 520 nm to selectively harden the second composition; and subsequently irradiating the first hardenable composition with radiation within a range of about 380 nm to about 520 nm to harden the first composition and adhere the second composition to the surface; wherein neither the first photoinitiator nor the second photoinitiator absorbs radiation above about 520 nm. As used herein, "selectively harden" means that the second composition is hardened while the first composition remains substantially unhardened.

In certain embodiments, the first hardenable composition is a dental adhesive and the second hardenable composition is a dental composite. In certain embodiments, the surface is an oral surface, typically a surface of a tooth or bone. In certain embodiments, the first photoinitiator is a phosphine oxide and the second photoinitiator is a diketone. Preferred phosphine oxides are acyl and bisacyl phosphine oxides, with the more preferred being bisacyl phosphine oxides. The photoinitiators of this invention preferably absorb light between about 380 to about 520 nm and are either nearly colorless, pale yellow, or yellow in coloration.

Examples of phosphine oxides include the acyl phosphine oxides of the formula:

wherein: each $R^1$ is individually a hydrocarbyl group, wherein optionally two $R^1$ groups can be joined to form a ring along with the phosphorous atom; and each $R^2$ is independently a hydrocarbyl group, an S—, O—, or N-containing five- or six-membered heterocyclic group, or a —Z—C(=O)P(=O)(R¹)₂ group, wherein Z represents a divalent hydrocarbyl group.

Examples of phosphine oxides also include the bisacyl phosphine oxides of the formula:

wherein: $R^1$ is a hydrocarbyl group; and each $R^2$ is independently a hydrocarbyl group, an S—, O—, or N-containing five- or six-membered heterocyclic group.

In another embodiment, a process for forming a dental material adhered to an oral surface includes: applying a hardenable dental adhesive to an oral surface, wherein the hardenable adhesive includes a first photoinitiator that absorbs radiation within a range of about 380 nm to about 450 nm; applying a hardenable dental composite to the hardenable dental adhesive on the oral surface, wherein the hardenable dental composite includes a second photoinitiator that absorbs radiation within a range of about 450 nm to about 520 nm; irradiating the hardenable dental composite with radiation within a range of about 450 nm to about 520 nm to selectively harden the hardenable dental composite; and subsequently irradiating the hardenable dental adhesive with radiation within a range of about 380 nm to about 450 nm to harden the adhesive and adhere the dental composite to the oral surface; wherein neither the first photoinitiator nor the second photoinitiator absorbs radiation above about 520 nm.

In yet another embodiment, a process for forming a dental material adhered to an oral surface includes: applying a hardenable dental adhesive to an oral surface, wherein the hardenable dental adhesive includes a phosphine oxide that absorbs radiation within a range of about 380 nm to about 450 nm; applying a hardenable dental composite to the hardenable dental adhesive on the oral surface, wherein the hardenable dental composite includes a diketone that absorbs radiation within a range of about 450 nm to about 520 nm; irradiating the hardenable dental composite with radiation within a range of about 450 nm to about 520 nm to selectively harden the dental composite; and subsequently irradiating the hardenable dental adhesive with radiation within a range of about 380 nm to about 450 nm to adhere the dental composite to the oral surface; wherein neither the first photoinitiator nor the second photoinitiator absorbs radiation above about 520 nm.

Each of the above embodiments includes at least two compositions, each of which includes at least one photoinitiator. Other embodiments in which only one or no photoinitiators are used are also included within the scope of the present invention.

In one such embodiment, the present invention provides a process for forming a dental material adhered to a surface that includes: applying a first hardenable dental composition to the surface; applying a second hardenable dental composition to the first hardenable dental composition on the surface; and hardening the first and second hardenable dental compositions to adhere the second composition to the surface, wherein the second hardenable composition is substantially completely hardened prior to complete hardening of the first hardenable composition; wherein at least one of the first or second hardenable compositions is chemically hardenable.

In another embodiment, the present invention provides a process for forming a dental material adhered to an oral surface that includes: applying a hardenable dental adhesive to the oral surface; applying a hardenable dental composite to the hardenable dental adhesive on the oral surface; and hardening the hardenable dental adhesive and hardenable dental composite to adhere the composite to the surface, wherein the hardenable dental composite is substantially completely hardened prior to complete hardening of the hardenable dental adhesive; wherein at least one of the hardenable adhesive or hardenable composite is chemically hardenable.

The present invention also provides devises that can be used to harden dental compositions, such as those of the present invention. In one embodiment, there is provided a dental composition hardening light that includes: a housing; a first light source located within the housing, the first light source emitting light in a first wavelength range; a second light source located within the housing, the second light source emitting light in a second wavelength range; and a controller operably connected to the first light source and the second light source, the controller controlling emission of light from the first light source and the second light source. Processes of hardening dental compositions using such lights are also encompassed by the present invention.

DETAILED DESCRIPTION OF PREFERRED EMBODIMENTS

The present invention provides processes for forming dental materials adhered to a surface. The surface is typically an oral surface such as the surface of a tooth or a bone, although other surfaces are encompassed, such as the surface of a fixture used to prepare a prosthetic device, for example.

The dental materials can be used for example, as dental adhesives, dental composites, artificial crowns, anterior or posterior fillings, casting materials, cavity liners, cements, coating compositions, mill blanks, restoratives, prostheses, and sealants. In a preferred aspect, the dental material is a dental restorative. The restoratives of the invention can be placed directly in the mouth and cured (hardened) in situ.

The processes involve applying a first hardenable dental composition (e.g., a dental adhesive) to the surface followed by applying a second hardenable dental composition (e.g., a dental composite) to the first hardenable dental composition on the surface. The first and second hardenable dental compositions are hardened such that the second hardenable composition is substantially completely hardened prior to complete hardening of the first hardenable composition. A "substantially completely hardened" composition is one that is sufficiently hard to support a load that would typically be applied in a dental environment.

In certain embodiments, both the first and second hardenable compositions include photopolymerizable materials. In other embodiments, at least one of the first or second hardenable compositions is chemically hardenable. In still other embodiments, both the first and second hardenable compositions are chemically hardenable. It is also envisioned that photopolymerizable materials and chemically hardenable materials can be combined in one composition if desired.

In the embodiments in which both the first and second hardenable compositions include photopolymerizable materials, the first hardenable composition includes a first photoinitiator that absorbs radiation within a range of about 380 nm to about 520 nm (alternatively, about 380 nm to about 450 nm) and the second hardenable composition includes a second photoinitiator that absorbs radiation within a range of about 380 nm to about 520 nm (alternatively, about 450 nm to about 520 nm). In these embodiments, neither the first photoinitiator nor the second photoinitiator absorbs radiation above about 520 nm.

If photoinitiators are used that absorb significant radiation above about 520 nm (e.g., ethyl eosin, erythrosine, and methylene blue), significant coloring can result and would be generally unacceptable in certain practical applications, e.g., as dental fillings and restorations. The photoinitiators of this invention preferably absorb light of about 380 nm to about 520 nm and are either nearly colorless, pale yellow, or yellow in coloration prior to and after irradiation with light of about 380 nm to about 520 nm.

The hardenable compositions of the present invention include compounds that are monomers, oligomers, polymers, or combinations thereof. Such materials are well known for both photopolymerizable dental compositions as well as chemically hardenable dental compositions. Typical polymerizable composition may also contain suitable additives such as fluoride sources, anti-microbial agents, accelerators, stabilizers, absorbers, pigments, dyes, viscosity modifiers, surface tension depressants and wetting aids, antioxidants, fillers, and other ingredients well known to those skilled in the art. The amounts and types of each ingredient should be adjusted to provide the desired physical and handling properties before and after polymerization.

Generally, dental compositions include fillers of the types described herein below. Depending on the type of resin system in the composition, e.g., cationically curable resins, different types of fillers are used. Depending on the type of composition, e.g., adhesive, different amounts of fillers are used. Such information is generally known to one of skill in the art. For example, adhesives and sealants are generally lightly filled (e.g., up to about 25 wt-% filler, based on the total weight of the composition) or unfilled. Cements often contain higher amounts of filler (e.g., about 25 wt-% to about 60 wt-% filler, based on the total weight of filler), and filling materials can contain even higher amounts of filler (e.g., about 50 wt-% to about 90 wt-% filler, based on the total weight of the composition).

Photopolymerizable Compositions

The hardenable compositions used in the methods of the present invention are in certain embodiments photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. Preferably, the irradiation has a functional wavelength range from about 380 nm to about 520 nm.

Suitable photopolymerizable compositions may include epoxy resins (which contain cationically active epoxy groups), vinyl ether resins (which contain cationically active vinyl ether groups), and ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof. Also suitable are polymerizable materials that contain both a cationically active functional group and a free radically active functional group in a single compound. Examples include epoxy-functional acrylates, epoxy-functional methacrylates, and combinations thereof.

Free Radically Photopolymerizable Compositions

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bisacrylates and bis-methacrylates of polyethylene glycols of molecular weight 200–500, copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

Cationically Photopolymerizable Compositions

Photopolymerizable compositions may include compounds having cationically active functional groups such as cationically polymerizable epoxy resins. Such materials include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Suitable epoxy-containing materials useful in the present invention are listed in U.S. Pat. No. 6,187,836 (Oxman et al.) and U.S. Pat. No. 6,084,004 (Weinmann et al.).

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable compositions may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to about 200, intermediate molecular weights, i.e. from about 200 to about 10,000, or high molecular weights, i.e. above about 10,000. As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below about 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The amount of hydroxyl-containing organic material used in the polymerizable compositions may vary over broad ranges, depending upon factors such as the compatibility of the hydroxyl-containing material with the cationically and/or free radically polymerizable component, the equivalent weight and functionality of the hydroxyl-containing material, the physical properties desired in the final composition, the desired speed of polymerization, and the like.

Blends of various hydroxyl-containing materials may also be used. Examples of such blends include two or more molecular weight distributions of hydroxyl-containing compounds, such as low molecular weight (below about 200), intermediate molecular weight (about 200 to about 10,000) and higher molecular weight (above about 10,000). Alternatively, or additionally, the hydroxyl-containing material may contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The polymerizable material(s) may also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, and tri-(meth)acrylate, sorbitol mono-, di-, tri-, tetra-, or penta-(meth)acrylate; and 2,2-bis[4-(2-hydroxy-3-methacryloxypropoxy)phenyl]propane.

The polymerizable material(s) may also contain hydroxyl groups and cationically active functional groups in a single molecule. An example is a single molecule that includes both hydroxyl groups and epoxy groups.

Photoinitiators

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, and diphenyliodonium tetrafluoroboarate. Preferred photosensitizers are monoketones and diketones that absorb some light within a range of about 450 nm to about 520 nm (preferably, about 450 nm to about 500 nm). More preferred compounds are alpha diketones that have some light absorption within a range of about 450 nm to about 520 nm (even more preferably, about 450 to about 500 nm). Preferred compounds are camphorquinone, benzil, furil, 3,3,6,6-tetramethylcyclohexanedione, phenanthraquinone and other cyclic alpha diketones. Most preferred is camphorquinone. Preferred electron donor compounds include substituted amines, e.g., ethyl dimethylaminobenzoate.

Suitable photoinitiators for polymerizing cationically photopolymerizable compositions include binary and tertiary systems. Typical tertiary photoinitiators include an iodonium salt, a photosensitizer, and an electron donor compound as described in U.S. Pat. No. 5,856,373 (Kaisaki et al.), U.S. Pat. No. 6,084,004 (Weinmann et al.), U.S. Pat. No. 6,187,833 (Oxman et al.), and U.S. Pat. No. 6,187,836 (Oxman et al.); and in U.S. Ser. No. 10/050,218 (Dede et al.;

filed Jan. 15, 2002). Preferred iodonium salts, photosensitizers, and electron donor compounds are as listed herein for photoinitiator systems for polymerizing free radically photopolymerizable compositions.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Köihler et al.); and EP Application No. 0 173 567 A2 (Ying).

Suitable acyl phosphine oxides have the general formula:

$$(R^1)_2P(=O)C(=O)R^2$$

wherein: each $R^1$ is individually is a hydrocarbyl group (e.g., alkyl, cycloalkyl, aryl, and aralkyl, any of which can be substituted with a halo, alkyl, or alkoxy group), wherein optionally two $R^1$ groups can be joined to form a ring along with the phosphorous atom; and each $R^2$ is independently a hydrocarbyl group, an S—, O—, or N-containing five-or six-membered heterocyclic group (aromatic or alicyclic), or a —Z—C(=O)P(=O)($R^1$)$_2$ group, wherein Z represents a divalent hydrocarbyl group such as alkylene or phenylene having from 2 to 6 carbon atoms.

Suitable bisacyl phosphine oxides have the general formula:

$$R^1P(=O)(C(=O)R^2)_2$$

wherein: $R^1$ is a hydrocarbyl group; and each $R^2$ is independently a hydrocarbyl group (e.g., alkyl, cycloalkyl, aryl, and aralkyl, any of which can be substituted with a halo, alkyl, or alkoxy group), an S-, O-, or N-containing five- or six-membered heterocyclic group (aromatic or alicyclic).

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Preferred acyl phosphine oxides useful in the present invention are those in which the $R^1$ and $R^2$ groups are phenyl, C1–C4 alkyl, or C1–C4 alkoxy-substituted phenyl. Most preferably, the acyl phosphine oxide is bis(2,4,6-trimethylbenzoyl)phenyl phosphine oxide (IRGACURE 819, Ciba Specialty Chemicals) or bis(2,6-dimethoxybenzoyl)-(2,4,4-trimethylpentyl) phosphine oxide (CGI 403, Ciba Specialty Chemicals)

Typically, the phosphine oxide initiator is present in the photopolymerizable composition in catalytically effective amounts, such as from about 0.1 weight percent to about 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from about 0.1 weight percent to about 5.0 weight percent, based on the total weight of the composition.

Photopolymerization Procedure and Device

The photopolymerizable compositions are typically prepared by admixing, under "safe light" conditions (i.e., conditions that do not cause premature hardening of the composition), the various components of the compositions. Suitable inert solvents may be employed if desired when preparing the mixture. Examples of suitable solvents include acetone and dichloromethane.

Hardening is affected by exposing the composition to a radiation source, preferably a visible light source. It may be convenient to employ light sources that emit visible light between about 380 nm and about 800 nm. In some instances, it may be possible to use light sources that emit light in a more restricted spectrum, e.g., blue light with wavelengths of about 380 nm to about 520 nm). Examples of some suitable light sources include, but are not limited to, quartz halogen lamps, tungsten-halogen lamps, mercury arcs, carbon arcs, low-, medium-, and high-pressure mercury lamps, plasma arcs, light-emitting diodes, and lasers.

In general, useful light sources may have intensities in the range of about 200 to about 1200 mW/cm². One example, which may be useful for dental applications, is a XL-3000 dental curing light commercially available from 3M Company of St. Paul, Minn. Such lights may, e.g., have an intensity of about 400 to about 800 mW/cm² at wavelengths of about 400 nm to about 500 nm.

The exposure may be affected in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity.

Where multiple exposures are employed, the intensity of each dosage may be the same or different. Similarly, the total energy of each exposure may be the same or different.

Because hardening of the hardenable compositions may be affected by exposure to light of different wavelengths, different devices, each providing light in the different wavelength ranges, could be used to effect selective hardening of the compositions. It may, however, be desirable to supply one device capable of selectively providing light in the different wavelength ranges such that a user need handle only one device during hardening. In other alternatives, that single device may be designed to automatically supply the different wavelengths for selected time intervals and at selected intensities.

Figure 1:
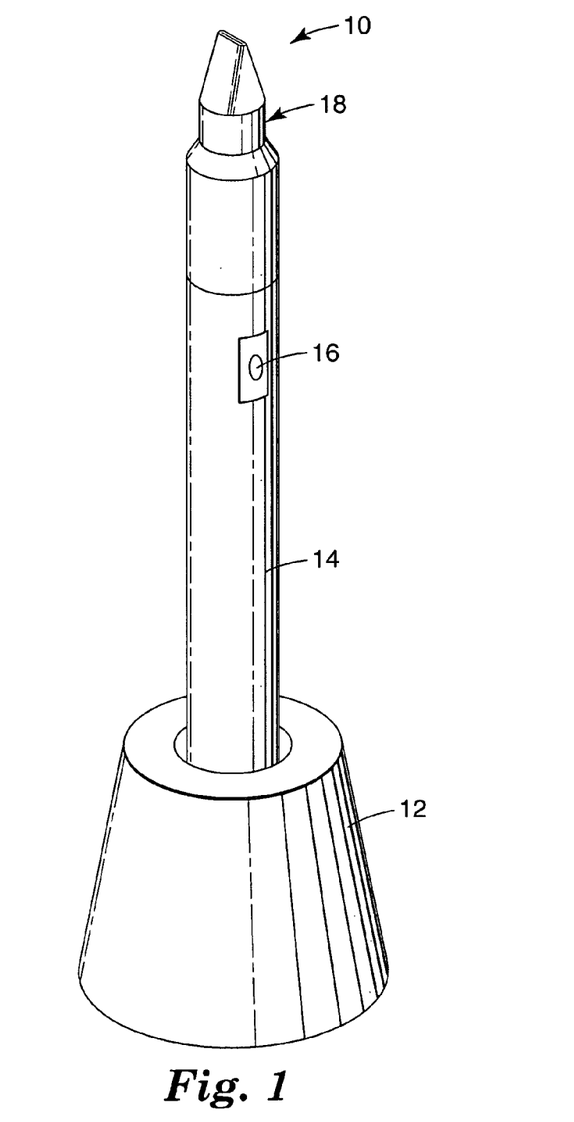
FIG. 1 is a perspective view of one illustrative device according to the present invention.

FIG. 1 depicts one illustrative embodiment of a hardening device 10 that may be used in connection with the present invention. The device 10 may be provided with a base 12 that can hold the device 10 in a convenient orientation and that may also serve as a charging stand if the device 10 is powered by batteries. The device 10 may include a housing 14 that may have a generally cylindrical shape as seen in FIG. 1. In the depicted embodiment, the device includes a switch 16 to activate one or more light sources such that light is delivered through the tip 18 of the device 10.

The depicted device 10 is to be considered exemplary in nature only. Other light sources that may be used in connection with hardenable dental compositions are described in, e.g., U.S. Pat. No. 4,516,195 (Gonser); U.S. Pat. No. 4,888,489 (Bryan); and U.S. Pat. No. 5,147,204 (Patten et al.); as well as in International Publication Nos. WO 99/22667 (Broyles et al.) and WO 01/64129 (Adam et al.).

Figure 2:
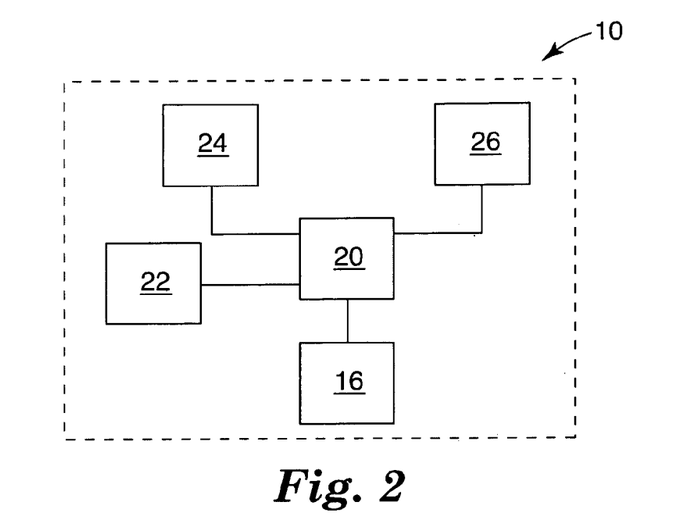
FIG. 2 is a block diagram of components in one illustrative hardening device according to the present invention.

Because the different hardenable compositions of the present invention harden in response to light of different wavelengths, it may be preferred that the device 10 be capable of selectively providing light in the different wavelengths needed to cure the different hardenable compositions. Turning to FIG. 2, a block diagram of the some of the components that may be contained within the device 10 are depicted. The device 10 preferably includes a switch 16 that can be used to activate the light source. The switch 16 is operatively connected to a controller 20 that is, in turn operatively connected to a pair of light sources 24 and 26. The controller 20 is also preferably connected to a power source 22 (e.g., battery, fuel cell, etc.) that preferably provides power to controller 20 and the light sources 24 and 26.

The light sources 24 and 26 may be limited to emitting light in selected wavelength ranges, and those ranges may or may not overlap. For example, the first light source 24 may emit light only within a first wavelength range (e.g., about 380 nm to about 450 nm), while the second light source may emit light only within the second wavelength range (e.g., about 450 nm to about 520 nm). Alternatively, one of the light sources may emit light in both the first and second wavelength ranges (or even broader, e.g., one of the light sources may emit broadband white light). In another alternative, the light sources may include filters to limit the wavelengths of light emitted. In still another variation, it may be possible to use a device including one light source emitting light over all desired wavelength ranges and one or more filters to selectively deliver light in selected wavelength ranges. One example of such a device may be described in, e.g., U.S. Pat. No. 4,516,195 (Gonser).

Although one system for providing light of different wavelengths is depicted in FIG. 2, it should be understood that many variations in the actual construction of a hardening device useful in connection with the present invention may be possible. For example, the switch 16 may be optional if activation of the device can be accomplished by other techniques (e.g., simply removing the device 10 from the stand 12 may trigger an internal switch to activate the device in some embodiments). In another alternative, the controller 20 may be integrated into the light sources 24 and 26. In still another potential variation, each light source 24 and 26 may be attached directly to the power source 22 or to their own individual power sources. Further, the controller 20 may be provided as, e.g., a digital microprocessor, analog circuit, or combination of digital and analog controls. Other variations in the particular arrangement and selection of components will be known to those skilled in the art.

Further, although the light sources 24 and 26 are depicted in FIG. 2 as separate and distinct components, it should be understood that they could be supplied together as an integrated component. One example of an integrated LED light source capable of providing light in different wavelengths is described in U.S. Patent Application Publication No. US 2001/0032985 A1 (Bhat et al.). Others will be known to those skilled in the art.

Figure 3:
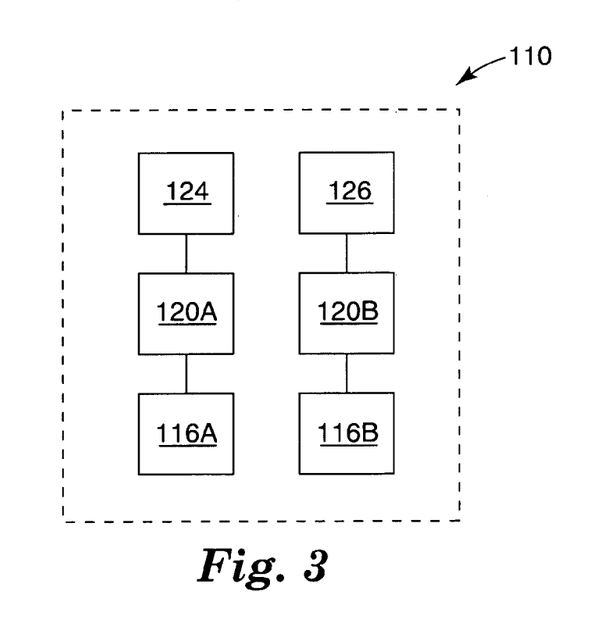
FIG. 3 is a block diagram of components of another illustrative hardening device according to the present invention.

FIG. 3 depicts a block diagram of one alternative hardening device 110 that may be used in connection with the present invention. In the device 110, two separate light sources 124 and 126 are each controlled by their own controllers 120a and 120b, respectively. Each of the controllers 120a and 120b is activated by a separate optional switch 116a and 116b, respectively. Such a system may be amenable to use in a manual light delivery protocol as discussed below.

In any hardening device used in connection with the present invention, a variety of different light delivery protocols may be used to deliver light of the selected wavelength ranges such that selective hardening of the hardenable compositions is achieved. In one example, the hardenable compositions may include a first hardenable composition with a first photoinitiator that absorbs radiation within a range of about 380 nm to about 450 nm and a second hardenable composition with a second photoinitiator that absorbs radiation within a range of about 450 nm to about 520 nm. In other words, a first hardenable composition hardens in response to light within a first wavelength range and a second hardenable composition hardens in response to light within a second wavelength range. In one light delivery protocol, the delivery of light to harden these hardenable compositions may involve initially providing light with a wavelength of about 450 nm or more to selectively harden the second hardenable composition. It may, in some instances, be desired to limit the upper end of the wavelength range to about 520 nm or less. With the second hardenable composition at least partially or fully hardened, light with a wavelength of about 450 nm or less may be provided to harden the first hardenable composition. It may, in some instances, be desired to limit the lower end of the wavelength range to about 380 nm or more. This light delivery protocol may be described as sequential, i.e., light within a second wavelength range is delivered for an initial interval and stopped, followed by delivery of light within a first wavelength range after termination of the initial interval.

In another light delivery protocol, the delivery of light to harden these hardenable compositions may involve initially providing light with a second wavelength range of about 450 nm or more such that the second hardenable composition can be selectively hardened (with the option of limiting the upper end of the second wavelength range to about 520 nm or less). With the second hardenable composition at least partially or fully hardened, light within a first wavelength range of about 450 nm or less may be provided to harden the first hardenable composition (with the option of limiting the lower end of the wavelength range to about 380 nm or more). The difference in this alternative is that delivery of light within the second wavelength range is not terminated during the delivery of light within the first wavelength range. As a result, the subsequent phase of light delivery includes light both above and below 450 nm (with optional lower and upper limits of about 380 nm and about 520 nm). This protocol for light delivery may be described as cumulative, i.e., light within a second wavelength range is delivered for an initial interval, followed by delivery of light within both the first and a second wavelength ranges after termination of the initial interval. In such a cumulative light delivery protocol, the second hardenable composition may be only partially hardened when only light in the second wavelength range is delivered, with complete hardening of the second hardenable composition occurring during delivery of light in both the first and second wavelength ranges.

These and other different light delivery protocols may preferably be automatically implemented by, e.g., a controller or controllers within a hardening device of the present invention. Alternatively, the different protocols may be manually implemented by a user activating light delivery in the different wavelengths during the hardening process.

Chemically Polymerizable Compositions

The hardenable compositions of the present invention are in certain embodiments, e.g., dental adhesive compositions, chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include glass ionomer cements, resin-modified glass ionomer cements, redox cure systems, and combinations thereof.

Glass Ionomer Cements

The chemically hardenable compositions may include conventional glass ionomers that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers typically are supplied in powder/liquid formulations that are mixed just before use. The mixture will undergo self-hardening in the dark due to an ionic reaction between the acidic repeating units of the polycarboxylic acid and cations leached from the glass.

Resin-Modified Glass Ionomer Cements

The chemically hardenable compositions may include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859, 089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g. as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski et al.). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. Ser. No. 09/916,399 (Mitra; Filed Jul. 27, 2001).

Redox Cure Systems

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Ser. No. 10/121,326 (Mitra et al.; Filed Apr. 12, 2002) and U.S. Pat. Ser. No. 10/121,329 (Mitra et al.; Filed Apr. 12, 2002).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Ser. No. 10/121,329 (Mitra et al.; Filed Apr. 12, 2002).

The reducing and oxidizing agents are present in an amount sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least about 0.01 wt-%, and more preferably at least about 0.1 wt-%, based on the total weight (including water) of the components of the polymerizable composition. Preferably, the reducing agent is present in an amount of no greater than about 10 wt-%, and more preferably no greater than about 5 wt-%, based on the total weight (including water) of the components of the polymerizable composition.

Preferably, the oxidizing agent is present in an amount of at least about 0.01 wt-%, and more preferably at least about 0.10 wt-%, based on the total weight (including water) of the components of the polymerizable composition. Preferably, the oxidizing agent is present in an amount of no greater than about 10 wt-%, and more preferably no greater than about 5 wt-%, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a glass ionomer cement and with a photopolymerizable composition such as described U.S. Pat. No. 5,154,762 (Mitra et al.).

The hardenable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

Fillers

The hardenable compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler is also substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

Preferably, the average particle size (typically, diameter) for the FAS glass is no greater than about 10 micrometers, and more preferably no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used either in the same part or in different parts.

Other suitable fillers are disclosed in U.S. Pat. No. 6,387,981 (Zhang et al.) as well as International Publication Nos. WO 01/30304 (Wu et al.), WO 01/30305 (Zhang et al.), WO 01/30306 (Windisch et al.), and WO 01/30307 (Zhang et al.).

U.S. Pat. No. 6,306,926 (Bretscher et al.) disclose a number of radiopacifying fillers that can be used in both free radically polymerizable compositions, cationically polymerizable compositions, and hybrid compositions featuring both free radically and cationically polymerizable components. They are particularly advantageous for use in cationically polymerizable compositions. One such filler is a melt-derived filler that includes 5–25% by weight aluminum oxide, 10–35% by weight boron oxide, 15–50% by weight lanthanum oxide, and 20–50% by weight silicon oxide. Another filler is a melt-derived filler that includes 10–30% by weight aluminum oxide, 10–40% by weight boron oxide, 20–50% by weight silicon oxide, and 15–40% by weight tantalum oxide. A third filler is a melt-derived filler that includes 5–30% by weight aluminum oxide, 5–40% by weight boron oxide, 0–15% by weight lanthanum oxide, 25–55% by weight silicon oxide, and 10–40% by weight zinc oxide. A fourth filler is a melt-derived filler that includes 15–30% by weight aluminum oxide, 15–30% by weight boron oxide, 20–50% by weight silicon oxide, and 15–40% by weight ytterbium oxide. A fifth filler is in the form of non vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or compound. A sixth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound.

Dental Adhesives

Numerous examples of hard tissue adhesives have been disclosed. For example, U.S. Pat. No. 4,719,149 (Aasen et al.) and references therein include a variety of materials and methods for adhering methacrylate-based composites to hard tissues. There are many other patents that describe various preferred materials and protocols for bonding to teeth, such as for example, U.S. Pat. No. 5,256,447 (Oxman et al.) and U.S. Pat. No. 5,525,648 (Aasen et al.). U.S. Pat. No. 5,980,253 (Oxman et al.) describes materials and methods for bonding cationically curable compositions to hard tissues. Also, siloxane-functional (meth)acrylates as disclosed in WO-00/38619 (Guggenberger et al.), WO-01/92271 (Weinmann et al.), WO-01/07444 (Guggenberger et al.), WO-00/42092 (Guggenberger et al.), and fluoropolymer-functional (meth)acrylates as disclosed in U.S. Pat. No. 5,076,844 (Fock et al.), U.S. Pat. No. 4,356,296 (Griffith et al.), EP-0373 384 (Wagenknecht et al.), EP-0201 031 (Reiners et al.), EP-0201 778 (Reiners et al.) can be used as dental adhesives.

Certain embodiments of the dental adhesives include at least one free radical inhibitor. The amount of inhibitor is sufficient to reduce the amount of cross-boundary polymerization. Examples include BHT (2,6-di-tert-butyl-4-methylphenol), MEHQ (methylethyl hydroquinone), and bisphenol-A. Typically, the inhibitor is used in an amount of about 0.05 wt-% to about 1.0 wt-%, based on the weight of the resin (e.g., adhesive composition without filler).

Such known materials can be used in the processes of the present invention. Generally, these materials have been used in processes that initially harden the adhesive and then the composite material. That is, conventional methods utilize one or more of the following steps: surface treatment of the tooth (e.g., etching, priming), application of a hardenable adhesive to the tooth surface, curing of the adhesive, placement of a composite material (e.g., restorative) on the hardened adhesive, and curing of the composite material. Such methods also typically utilize a blue light source emitting between approximately 380 nm to 520 nm to induce hardening.

In contrast, according to the present invention the composite material is substantially completely hardened prior to complete hardening of the adhesive. For example, in one embodiment, the hardenable adhesive includes a first photoinitiator that absorbs radiation within a range of about 380 nm to about 450 nm (e.g., a phosphine oxide), is irradiated only after the hardenable dental composite, which includes a second photoinitiator that absorbs radiation within a range of about 450 nm to about 520 nm, is hardened. This occurs through the use of two photoinitators that absorb radiation at different wavelengths, such that the hardening process can be controlled through the separate and sequential use of two different wavelengths of irradiation.

Dental Composites

The composites of the present invention are generally considered to be highly filled compositions and are typically hardened (e.g., polymerized or cured) using either free radical and or cationic photoinitiator systems, e.g., the ternary photoinitiator systems described herein. When cured the composites are effective as filling or restorative materials to fill a hole, crack, or cavity, e.g., a cavity within a tooth.

Preferred composite materials include methacrylate and epoxy compositions as well as glass ionomers that include polyacrylic acids, water, FAS glasses, and optionally free radically polyermizable resins and polymerization catalysts such as described in U.S. Pat. No. 6,306,926 (Bretscher et al.) and U.S. Pat. No. 6,030,606 (Holmes).

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

| Abbreviations, Descriptions, and Sources of Materials | | |
| --- | --- | --- |
| Abbreviation | Description | Source |
| Bis-GMA | 2,2-Bis[4-(2-hydroxy-3-methacryloyloxy-propoxy)phenyl]propane | CAS No. 1565-94-2 |
| EDMAB | Ethyl 4-dimethylaminobenzoate | Sigma-Aldrich (St. Louis, MO) |
| BHT | 2,6-Di-tert-butyl-4-methylphenol | Sigma-Aldrich |

-continued

Abbreviations, Descriptions, and Sources of Materials

| Abbreviation | Description | Source |
|---|---|---|
| HEMA | 2-Hydroxyethyl methacrylate; contains 150 ppm 4-methoxyphenol as an inhibitor. | Sigma-Aldrich |
| CPQ | Camphorquinone visible light sensitizer | Sigma-Aldrich |
| OMAN 072 | $SbF_6$ iodonium salt | Gelest, Tullytown, PA |
| IRGACURE 819 | Phosphine oxide initiator | Ciba Specialty Chemicals Corp., Terrytown, NY |
| Z100 | Dental restorative (A3 Shade) (Contains CPQ sensitizer) | 3M Company, St. Paul, MN |
| P-60 | Dental restorative (Contains CPQ sensitizer) | 3M Company |
| DPI HFP | Diphenyliodonium hexafluorophosphate | Johnson Matthey, Alpha Aesar Division, Ward Hill, NJ |
| TEGDMA | Triethylene glycol dimethacrylate | Sartomer Co., West Chester, PA |
| BPO | Benzoyl Peroxide | Sigma-Aldrich |
| DHEPT | N,N-Bis(2-hydroxyethyl)-p-toluidine | Sigma-Aldrich |
| Tinuvin P | 2-(2'-hydroxy-5'-methylphenyl)-benzotriazole; UV inhibitor | Ciba Specialty Chemicals Corp. |
| BME | Benzoin methyl ether (2-methoxy-2-phenylacetophenone) | Ciba Specialty Chemicals Corp. |
| MDEA | Methyldiethanolamine | Sigma-Aldrich |
| Eosin Y | 2',4',5',7'-Tetrabromofluorescein, disodium salt | Sigma-Aldrich |

Test Methods

Shear Bond Strength: Shear bond strength was evaluated by mounting the tooth sample in a holder clamped in the jaws of an "Instron" apparatus with the tooth surface (dentin or enamel) oriented parallel to the direction of pull. A loop of orthodontic wire (0.44-mm diameter) was placed around the hardened restorative material that was bound to the tooth surface. The ends of the orthodontic wire were clamped in the pulling jaw of the Instron apparatus, thereby placing the bond in shear stress. The bond was stressed using a crosshead speed of 2 mm/min until the restorative material separated from the tooth surface. The force (in MPa) required to break the bond was reported as an average of 5 samples.

Tooth Strain: Strain measurements of restored teeth using strain gauges were conducted according to the methodology described in the following publications: Morin D, DeLong R, Douglas W H, Cusp reinforcement by the acid-etch technique, J Dent Res 1984, 63: 1075–1078; Morin D L, Douglas W H, Cross M, DeLong R, Biophysical stress analysis of restored teeth: experimental strain measurement, Dent Mater 1988, 4: 41–48; Lopes L M P, Leitao J G M, Douglas W H, Effect of a new resin inlay/only restorative material on cuspal reinforcement, Quintessence Int 1991, 22: 641–645.

Briefly, strain gauges (Type CEA-06-032UW-120, Measurements Group, Inc., Micro-Measurements Division, Raleigh, N.C.) were bonded to opposite sides of extracted human teeth (premolars) cut with a mesial-occlusal-distal (MOD) setup for subsequent restoration utilizing methods of the present invention. The bonding was achieved with M-Bond 200 Adhesive Kit (Measurements Group, Inc., M-Line Accessories, Raleigh, N.C.). The strain gauges were connected to a strain conditioner (Eight-Channel 2100 System, Measurements Group, Inc., Instruments Division, Raleigh, N.C.) using a quarter-bridge circuit layout (external dummy). The strain conditioner was connected to a PC (Slimline-325 (386), Northgate Computer Systems, Northgate Innovations, Inc., City of Industry, Calif.; Acquisition Software Program: Labtech Notebook (version 6.2.0), Adept Scientific Inc., Bethesda, Md.) for real-time acquisition of both strain guage channels versus time at 5 Hz for 300 seconds per measurement. Results for various restoration procedures were reported in "microstrain" units with larger values indicative of greater tooth stress and strain within the restoration.

Adhesive Compositions

Adhesive A: An adhesive composition was prepared by combining a 65/35 weight-% blend of bis-GMA/HEMA with CPQ (0.5%), EDMAB (0.5%), and OMAN 072 $SbF_6$ iodonium salt (0.5%). The composition was designated Adhesive A.

Adhesives B–H: An adhesive composition was prepared by combining a 65/35 weight-% blend of bis-GMA/HEMA with IRGACURE 819 (1.5%) and BHT inhibitor (0.5%). The composition was designated Adhesive B. Adhesives C–H were prepared as described for Adhesive B, except with different concentration levels of IRGACURE 819 and BHT as shown in Table 1.

TABLE 1

Compositions of Adhesives B–H.

| Adhesive | % BHT | % IRGACURE 819 |
|---|---|---|
| B | 0.5 | 1.5 |
| C | 0.2 | 1.5 |
| D | 0.1 | 0.5 |
| E | 0.1 | 1.5 |
| F | 0.025 | 0.5 |
| G | 0.0625 | 1.0 |
| H | 0.025 | 1.5 |

Adhesive I: An adhesive composition was prepared by combining a 60/40 weight-% blend of bis-GMA/HEMA with IRGACURE 819 (0.5%) and BHT inhibitor (0.1%). The composition was designated Adhesive I.

Example 1

Selective Curing of Compositions Having Different Photoinitiator Systems

The objective of this example was to demonstrate that compositions having different photoinitiator systems could be selectively cured (i.e., polymerized to a hardened material) with applied light having different effective wavelength ranges. An additional objective was to measure shear bond strength of sequentially irradiated tooth samples coated with various adhesive compositions and filled with a dental restorative.

Enamel and dentin tooth samples were prepared in a conventional manner by grinding with standard 120 grit/600 grit, etching with SCOTCHBOND phosphoric acid etchant (3M Company), and priming with SCOTCHBOND multi-purpose primer (3M Company). A thin coating of Adhesive A or Adhesive B was then applied to separately prepared tooth samples and left uncured. A Teflon mold 2.5-mm thick and having a cylindrical 4-mm diameter hole was placed over each adhesive-coated tooth sample and filled with Z100 dental restorative. The adhesive-coated and restorative-filled tooth samples were then irradiated by one of the following two curing methods:

Curing Method 1. The tooth samples were irradiated by exposure at 50 mw/cm² for 10 seconds to an ACCUCURE 3000 Laser (Lasermed, Salt Lake City, Utah) having an effective wavelength range of about 460–500 nm. Radiation at this wavelength range would be expected to cure materials having CPQ-based photoinitiator systems that generally cure within a wavelength range of about 400–500 nm, but would not be expected to cure materials having IRGACURE 819 photoinitiator systems that generally cure within a wavelength range of about 380–450 nm.

Curing Method 2. The tooth samples were irradiated by Curing Method 1 and then subsequently irradiated by exposure at 800 mw/cm² for 20 seconds to a VISILUX 2500 halogen light (3M Company) having an effective wavelength range of about 400–500 nm. Radiation at this wavelength range would be expected to cure materials having either CPQ-based or IRGACURE 819 photoinitiator systems.

Shear Bond Strength Determinations. The irradiated tooth samples were then evaluated for shear bond strength according to the Shear Bond Strength Test Method described herein and the results are reported in Table 2. High bond strength is generally achieved when both the adhesive layer and the restorative are in a cured (i.e., hardened) state.

In the case of tooth samples irradiated by Curing Method 1 (curing at about 460–500 nm), high bond strength was achieved with Adhesive A (containing CPQ) and Z100 (containing CPQ) (Run 1), but not with Adhesive B (containing IRGACURE 819) and Z100 (Runs 2 and 3). It is concluded that irradiating at 460–500 nm cured Adhesive A and Z100 restorative, but did not cure Adhesive B.

In the case of tooth samples irradiated by Curing Method 2 (irradiating at about 460–500 nm followed by irradiating at about 400–500 nm), high bond strength was achieved with both Adhesive A/Z100 and Adhesive B/Z100 combinations (Runs 4–6). It is concluded that curing by this method first cured Adhesive A and Z100 restorative (at 460–500 nm) and then cured Adhesive B (at 400–500 nm).

TABLE 2

Shear Bond Strength of Adhesive-Coated, Z100 Composite-Filled Tooth Samples Following Irradiation.

| Run | Substrate | Adhesive | Photoinitiator System In Adhesive | Curing Method | Shear Bond Strength MPa (SD) |
| --- | --- | --- | --- | --- | --- |
| 1 | Enamel | Adhesive A | CPQ-Based | 1 | 18.9 (4.3) |
| 2 | Enamel | Adhesive B | IRGACURE 819 | 1 | 1.9 (1.8) |
| 3 | Dentin | Adhesive B | IRGACURE 819 | 1 | 0.5 (0.7) |
| 4 | Enamel | Adhesive A | CPQ-Based | 2 | 20.6 (3.8) |
| 5 | Enamel | Adhesive B | IRGACURE 819 | 2 | 16.9 (5.6) |
| 6 | Dentin | Adhesive B | IRGACURE 819 | 2 | 12.4 (4.6) |

Example 2

Selective Curing of Compositions Having Different Photoinitiator Systems

A layer of Adhesive A or Adhesive B was coated on separate glass slides followed by the addition of a Z100 restorative layer to each adhesive layer. Following irradiation of the coated slides with an ACCUCURE 3000 Laser as described in Example 1 (Curing Method 1), the Z100 layer could be moved readily on the Adhesive B-coated slide; whereas, the Z100 layer was firmly adhered to the Adhesive A-coated slide. Subsequent irradiation with a VISILUX 2500 halogen light as described in Example 1 (Curing Method 2) caused the Z100 layer to become firmly adhered to the Adhesive B-coated slide.

Example 3

Selective Curing of Compositions Having Different Photoinitiator Systems

An aliquot of Adhesive A or Adhesive B was added to separate glass vials followed by the addition of an aliquot of P-60 restorative to each vial. Following irradiation of the filled vials for 15 seconds with the ACCUCURE 3000 Laser, the P-60 restorative cured to a solid polymer in a solidified Adhesive A; whereas in the other vial, the P-60 solid polymer was surrounded by a still fluid Adhesive B. Subsequent irradiation with a VISILUX 2500 halogen light as described in Example 1 (Curing Method 2) would be expected to solidify Adhesive B.

It is concluded from the results of Examples 2 and 3 that irradiation at a wavelength range of 460–500 cured Adhesive A and Z100 restorative (both with CPQ-based photoinitiator systems), but not Adhesive B (with IRGACURE 819); and that subsequent irradiation at a wavelength range of 400–500 cured or would cure Adhesive B.

Example 4

Effect of BHT/IRGACURE 819 Concentrations on Selective Curing

Aliquots of Adhesives B–H were separately placed on glass slides and irradiated with an ACCUCURE 3000 Laser as described in Example 1 (Curing Method 1). The adhesive compositions did not cure to a hardened state.

Thin layers of Adhesives B–H were then coated on separate glass slides followed by the addition of a Z100 restorative layer to each adhesive layer. Following irradiation of the coated slides with an ACCUCURE 3000 Laser as described in Example 1 (Curing Method 1), the cured solid Z100 layers on Adhesive D–H layers were adhered to the glass slides; whereas, the cured solid Z100 layers on Adhesives B–C did not adhere to the glass slides. The adherence of the Z100 layers with the Adhesive D–H layers may be attributed to cross-boundary cure (i.e., polymerization) initiated by the Z100 cure and may have occurred due to insufficient BHT free radical inhibitor in the Adhesives. In contrast, the lack of adherence of the Z100 layers with the Adhesive B–C layers suggests that sufficient BHT inhibitor was present in these adhesives to prevent or minimize cross-boundary cure from the Z100 cure. Subsequent irradiation with a VISILUX 2500 halogen light as described in Example 1 (Curing Method 2) did cause the Z100 layers to be adhered to the Adhesive B- and Adhesive C-coated slides.

It is concluded from the results of this Example that the level of free radical inhibitor in adhesive compositions based on phosphine oxide photoinitiators may be important in achieving the intended results with sequentially cured restorative-adhesive procedures.

Example 5

Effect on Tooth Strain Following Selective Curing

Extracted human teeth (premolars) were cut with a MOD (mesial, occlusal, distal) preparation as well known in the dental field and strain gauges were attached to opposite sides of the tooth structures in order to measure tooth displacement during and following irradiation as detailed in the Tooth Strain Test Method described herein. The tooth samples were prepared in a conventional manner by etching for 10–20 seconds with SCOTCHBOND phosphoric acid etchant and priming with SCOTCHBOND multi-purpose primer. A thin coating of Adhesive B was then applied to the prepared tooth cavities and subsequent steps were followed according to one of the following two protocols:

Standard (Conventional) Protocol: The adhesive-coated tooth cavity was irradiated by exposure at 800 mw/cm2 for 20 seconds to an ELIPAR Trilight (3M Company) having an effective wavelength range of about 400–500 nm. The adhesive layer cured to a hard coating. The cavity was then filled with Z100 restorative and irradiated for 60 seconds with the same light to cure the restorative.

Two-Wavelength Protocol: The adhesive-coated (uncured) tooth cavity was filled with Z100 restorative and the filled tooth irradiated by exposure at 800 mw/cm$^2$ for 60 seconds to an ELIPAR Trilight filtered with an Oriel 51290 light filter (Oriel, Stratford, Conn.) having a 475-nm cutoff to afford an effective wavelength range of about 475–500 nm. At this wavelength range the restorative was cured, whereas the Adhesive B layer was uncured. The Adhesive B layer was then cured by irradiating the filled tooth sample for 20 seconds with the ELIPAR Trilight absent the Oriel filter.

For both the Standard and the Two-Wavelength Protocols, tooth strain vs. time was measured during curing and post-curing according to the Tooth Strain Test Method described herein. Results in terms of "ultimate strain" after 5 minutes from the start of the initial irradiation was about 200 microstrain for the Standard Protocol and about 50 microstrain for the Two-Wave Protocol. Therefore, it can be concluded from the results of this example that the Two-Wave Protocol provided a 75% reduction in tooth strain as compared to the Standard Protocol.

Example 6

Sequential Curing of Compositions with Different Cure Mechanisms

The objective of this example was to demonstrate the sequential cure of an adhesive layer and subsequently applied composite layer utilizing different cure methods, e.g., a chemical cure (self-cure) mechanism for the composite layer followed by a photocure mechanism for the adhesive layer.

Bovine tooth samples embedded in an acrylic resin were prepared with 120-grit sandpaper such that a smooth and uniform enamel surface was obtained. SCOTCHBOND phosphoric acid etchant (3M Company) was applied by brush to groups of 5 teeth and allowed to reside on the surface of the teeth of about 15 seconds. The teeth were thoroughly rinsed with water to remove excess etching gel and then dried with a stream of compressed air.

Teflon molds 2.5-mm thick and having cylindrical 4.7-mm diameter holes fitted with gelatin capsule sleeves were applied, centered, and clamped directly onto the etched enamel surfaces of the teeth. The light curable Adhesive I composition (containing IRGACURE 819 photoinitiator) was applied with a brush as a thin film layer to the enamel surfaces directly below the holes of each Teflon mold. A two-part, self-curing (i.e., chemically polymerizable using a redox cure system) composite material made from the Paste A and Paste B components listed in Table 3 was then utilized as described in the following 3 curing methods.

TABLE 3

Components of Composite Material
Composite Material

| Paste A | | Paste B | |
| --- | --- | --- | --- |
| Component | Parts by Wt. | Component | Parts by Wt. |
| Bis-GMA | 18.83 | Bis-GMA | 18.16 |
| TEGDMA | 3.75 | TEGDMA | 3.63 |
| BHT | 0.13 | DHEPT | 0.53 |
| BPO | 0.029 | TINUVIN P | 0.18 |
| Quartz Fillers | 77.00 | Quartz Fillers | 77.50 |

Curing Method 1. The coated adhesive layer was irradiated for 30 seconds with an XL 3000 Dental Curing Light (3M Company) having an effective wavelength range of about 400–500 nm. The adhesive layer was thereby cured to a hardened coating. Equal portions of Paste A and Paste B were then mixed on a dental mixing pad until homogeneous and then increments of the resulting composite material were transferred to the holes in the Teflon molds until the molds were filled. The composite material hardened to the touch within 3 minutes. The samples were allowed to cure for a total of 5 minutes and the entire molds then immersed in water at 37° C. for 24 hours.

Curing Method 2. This method was identical to Curing Method 1, except that the coated adhesive layer was not irradiated with light (i.e., was left uncured) before the composite material was added to the molds.

Curing Method 3. This method was identical to Curing Method 2, except that directly following the 5-minute cure of the composite material, the samples were irradiated for 30 seconds with an XL 3000 Dental Curing Light by applying the light in direct contact with the cured composite material. The samples were allowed to cure and the entire molds then immersed in water at 37° C. for 24 hours.

Five samples for each curing method were then evaluated for Shear Bond Strength according to the test method described herein and the results (adhesion to enamel as an average of the 5 samples) were as follows:

Curing Method 1 Samples: 8.3±3.1 MPa

Curing Method 2 Samples: 1.9±2.3 MPa (4 out of the 5 samples exhibited no adhesion)

Curing Method 3 Samples: 14.9±3.5 MPa

It can be concluded from these results that the greatest adhesion to enamel was achieved with Curing Method 3 in which the composite material was cured by way of a self-cure mechanism (i.e., chemical polymerization) followed by a light cure of the adhesive layer (i.e., photopolymerization). This adhesion value (14.9±3.5 MPa) was nearly twice the adhesion achieved with Curing Method 1 in which the adhesive layer was cured by light before the addition and subsequent self-cure of the composite material. As expected, little or no adhesion was achieved with Curing Method 2 in which the adhesive layer was uncured.

Comparative Example 1

Utilization of Red Photoinitiator with Absorption Above 520 nm

The objective of this example was to demonstrate the physical properties (e.g., color) of sequentially cured layered compositions having different photoinitiator systems in different layers and having one of the photoinitiators capable of absorbing radiation at wavelengths greater than about 520 nm.

Compositions A (with Eosin Y, a red compound) and B (with CPQ) were prepared by combining the components listed in Table 4.

TABLE 4

Components of Compositions A and B

| Component | Composition A (Parts by Weight) | Composition B (Parts by Weight) |
|---|---|---|
| Bis-GMA/TEGDMA (50/50 Blend) | 9.89 | 9.5 |
| MDEA | 0.118 | 0.177 |
| BME | — | 0.32 |
| CPQ | 0.03 | — |
| Eosin Y | — | 0.005 |
| Silane-treated quartz filler | 40.15 | 40.01 |

A TEFLON mold having a cylindrical hole (6.5-mm deep and 6.3-mm diameter) was filled at the bottom (about 2-mm in thickness) with Composition B (having CPQ photosensitizer that absorbs radiation and promotes cure at a wavelength range of 400 to about 500 nm) and at the top (about 4.5-mm in thickness) with the pink Composition A (having Eosin Y photosensitizer that absorbs radiation and promotes cure at a wavelength range of about 450 to about 570 nm). Two additional Teflon molds were filled in the same manner. The first filled mold was irradiated from the top for 10 seconds with a 100 W high pressure Hg light source (Lesco, Torrance, Calif.) with a light intensity in the visible region in excess of 200 mW/cm2 and with the light filtered with an OG 515 long-pass glass filter (ESCO Products, Oak Ridge, N.J.) to provide a wavelength range that begins at about 480 nm and typically reaches about 50% transmittance at about 515 nm. The first mold was then irradiated from the top again for 10 seconds in the same manner, except that an OG 400 long-pass filter (ESCO Products) was utilized to provide a wavelength range that begins at about 380 nm and typically reaches about 50% transmittance at about 400 nm. The second mold was irradiated twice in the same manner except that the irradiation times were both 20 seconds and the third mold was irradiated twice in the same manner except that the irradiation times were both 40 seconds.

For all 3 mold samples the top layer of Composition A hardened during the first irradiation with the OG 515 filter, but Composition B remained uncured. Composition B then hardened during the second irradiation with the OG 400 filter. In all cases the Composition A in the mold changed color from pink to yellow-orange following curing. In contrast, the Composition B in the mold remained a light yellow following curing. Significant coloring following curing would be generally unacceptable in certain practical applications, e.g., as dental fillings and restorations.

The Barcol Hardness of the cured compositions was determined with a Barcol Hardness Tester (Model GYZJ 934-1, Barber-Colman Company, Loves Park, Ill.) used according to manufacturer's instructions and the results are provided in Table 5. It can be concluded from the data in Table 5 that increasing the irradiation times from 10 to 40 seconds led to a more complete cure (i.e., hardening) of the bottom composition layer, whereas the top layer was essentially completely cured at all irradiation times.

TABLE 5

Barcol Hardness Results

| Teflon Mold | Irradiation Time (Seconds) | Barcol Hardness Units | |
|---|---|---|---|
| | | Top Layer (with Eosin Y) | Bottom Layer (with CPQ) |
| First | 2 × 10 | 80 | 12–15 |
| Second | 2 × 20 | 85 | 60 |
| Third | 2 × 40 | 88 | 80 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A process for forming a dental material adhered to an oral surface, the process comprising:
    applying a hardenable dental adhesive to an oral surface, wherein the hardenable adhesive comprises a first photoinitiator that absorbs radiation within a range of about 380 nm to about 450 nm;
    applying a hardenable dental composite to the hardenable dental adhesive on the oral surface, wherein the hardenable dental composite comprises a second photoinitiator that absorbs radiation within a range of about 450 nm to about 520 nm;
    irradiating the hardenable dental composite with radiation within a range of about 450 nm to about 520 nm to selectively harden the hardenable dental composite; and
    subsequently irradiating the hardenable dental adhesive with radiation within a range of about 380 nm to about 450 nm to harden the dental adhesive and adhere the dental composite to the oral surface;
    wherein neither the first photoinitiator nor the second photoinitiator absorbs radiation above about 520 nm.

2. The process of claim 1 wherein the hardenable dental adhesive comprises a free radically polymerizable composition, a cationically polymerizable composition, or combinations thereof.

3. The process of claim 1 wherein the hardenable dental adhesive, hardenable dental composite, or both further comprises a filler.

4. The process of claim 1 wherein the first photoinitiator comprises a phosphine oxide.

5. The process of claim 4 wherein the phosphine oxide is selected from the group consisting of acyl and bisacyl phosphine oxides.

6. The process of claim 5 wherein the phosphine oxide is a bisacyl phosphine oxide of the general formula:

wherein:
$R^1$ is a hydrocarbyl group; and
each $R^2$ is independently a hydrocarbyl group, an S—, O—, or N-containing five-or six-membered heterocyclic group.

7. The process of claim 6 wherein the phosphine oxide is bis(2,4,6-trimethylbenzoyl)phenyl phosphine oxide, bis(2,6-dimethoxybenzoyl)-(2,4,4-trimethylpentyl) phosphine oxide, or a combination thereof.

8. The process of claim 1 wherein the second photoinitiator comprises a monoketone, diketone, or combinations thereof.

9. The process of claim 8 wherein the second photoinitiator is selected from the group consisting of camphorquinone, benzil, furil, 3,3,6,6-tetramethylcyclohexanedione, phenanthraquinone, and combinations thereof.

10. The process of claim 9 wherein the second photoinitiator is camphorquinone.

11. The process of claim 1 wherein the dental adhesive comprises a free radical inhibitor.

12. The process of claim 11 wherein the free radical inhibitor is preset in an amount of about 0.05 wt-% to about 1.0 wt-% based on the weight of the dental adhesive without filler.

13. The process of claim 1 wherein the photoinitiators are nearly colorless, pale yellow, or yellow in coloration prior to and after irradiation with light having a wavelength range of about 380 nm to about 520 nm.

14. The process of claim 1 wherein the hardenable dental adhesive comprises a siloxane-functional (meth)acrylate, a fluoropolymer-functional (meth)acrylate, or a combination thereof.

15. The process of claim 1 wherein the hardenable dental composite comprises a free radically polymerizable composition, a cationically polymerizable composition, or combinations thereof.

16. A process for forming a dental material adhered to an oral surface, the process comprising:
applying a hardenable dental adhesive to an oral surface, wherein the hardenable dental adhesive comprises a phosphine oxide that absorbs radiation within a range of about 380 nm to about 450 nm;
applying a hardenable dental composite to the hardenable dental adhesive on the oral surface, wherein the hardenable dental composite comprises a diketone that absorbs radiation within a range of about 450 nm to about 520 nm;
irradiating the hardenable dental composite with radiation within a range of about 450 nm to about 520 nm to selectively harden the dental composite; and
subsequently irradiating the hardenable dental adhesive with radiation within a range of about 380 nm to about 450 nm to adhere the dental composite to the oral surface;
wherein neither the Phosphine oxide nor the diketone absorbs radiation above about 520 nm.

17. The process of claim 16 wherein the phosphine oxide and the diketone are nearly colorless, pale yellow, or yellow in coloration prior to and after irradiation with light having a wavelength range of about 380 nm to about 520 nm.

18. The process of claim 16 wherein the hardenable dental adhesive comprises a siloxane-functional (meth)acrylate, a fluoropolymer-functional (meth)acrylate, or a combination thereof.

19. The process of claim 16 wherein the phosphine oxide is selected from the group consisting of acyl and bisacyl phosphine oxides.

20. The process of claim 19 wherein the phosphine oxide is a bisacyl phosphine oxide of the general formula:

wherein: $R^1$ is a hydrocarbyl group; and
each $R^2$ is independently a hydrocarbyl group, en S—, O—, or N-containing five-or six-membered heterocyclic group.

21. The process of claim 20 wherein the phosphine oxide is bis(2,4,6-trimethylbenzoyl)phenyl phosphine oxide, bis(2,6-dimethoxybenzoyl)-(2,4,4-trimethylpentyl) phosphine oxide, or a combination thereof.

22. The process of claim 16 wherein the diketone is selected from the group consisting of camphorquinone, benzil, furil, 3,3,6,6-tetramethylcyclohexanedione, phenanthraquinone, and combinations thereof.

23. The process of claim 22 wherein the photoinitiator is camphorquinone.

24. The process of claim 16 wherein the dental adhesive comprises a free radical inhibitor.

25. The process of claim 24 wherein the free radical inhibitor is present in an amount of about 0.05 wt-% to about 1.0 wt-% based on the weight of the dental adhesive without filler.

* * * * *

UNITED STATES PATENT AND TRADEMARK OFFICE
CERTIFICATE OF CORRECTION

PATENT NO. : 7,134,875 B2  
APPLICATION NO. : 10/185431  
DATED : November 14, 2006  
INVENTOR(S) : Joel D. Oxman Page 1 of 1

It is certified that error appears in the above-identified patent and that said Letters Patent is hereby corrected as shown below:

Title Page, page 2  
Under "Item (56). References Cited, under OTHER PUBLICATIONS, 9th item listed on page 2, delete "Gernab" and insert in place thereof --German--.

Column 9  
Line 15, delete "(Köihler" and insert in place thereof --(Köhler--.

Column 18  
Line 42, delete "polymermizable" and insert in place thereof --polymerizable--.

Column 20  
Line 7, delete "guage" and insert in place thereof --gauge--.

Column 27  
Line 26, delete "preset" and insert in place thereof --present--.

Column 28  
Line 9, delete "Phosphine" and insert in place thereof --phosphine--.  
Line 29, delete "en" and insert in place thereof --an--.  
Line 41, delete "photoinitiator" and insert in place thereof --diketone--.

Signed and Sealed this

Fifteenth Day of May, 2007

JON W. DUDAS  
*Director of the United States Patent and Trademark Office*